(12) United States Patent
Rodier et al.

(10) Patent No.: US 7,235,214 B2
(45) Date of Patent: Jun. 26, 2007

(54) SYSTEM AND METHOD FOR MEASURING MOLECULAR ANALYTES IN A MEASUREMENT FLUID

(75) Inventors: Daniel Rodier, Louisville, CO (US); Scott Waisanen, Louisville, CO (US); Dale Griffin, Loveland, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 512 days.

(21) Appl. No.: 10/421,089

(22) Filed: Apr. 23, 2003

(65) Prior Publication Data

US 2004/0214334 A1 Oct. 28, 2004

(51) Int. Cl.
*B32B 5/02* (2006.01)
*B32B 27/04* (2006.01)
*B32B 27/12* (2006.01)
*G01N 7/00* (2006.01)
*G01N 21/00* (2006.01)

(52) U.S. Cl. ............................. 422/83; 422/88; 422/98; 422/101; 436/43; 436/149; 438/48; 438/49; 438/50; 702/1; 702/22; 702/23; 702/30; 702/31; 702/32

(58) Field of Classification Search ................ 422/83, 422/88, 98, 101; 436/43, 149; 438/48, 49, 438/50; 702/1, 22, 23, 30, 31, 32
See application file for complete search history.

(56) References Cited

U.S. PATENT DOCUMENTS

| | | | | |
|---|---|---|---|---|
| 3,956,032 A | * | 5/1976 | Powell et al. ................ | 117/101 |
| 4,446,720 A | * | 5/1984 | Sinclair ..................... | 73/24.06 |
| 4,818,348 A | * | 4/1989 | Stetter ........................ | 205/780 |
| 5,476,002 A | * | 12/1995 | Bowers et al. ............. | 73/24.01 |
| 5,661,226 A | * | 8/1997 | Bowers et al. ............. | 73/24.01 |
| 5,856,198 A | * | 1/1999 | Joffe et al. .................. | 436/100 |
| 5,918,258 A | * | 6/1999 | Bowers ..................... | 73/24.06 |

* cited by examiner

*Primary Examiner*—Brian Sines
(74) *Attorney, Agent, or Firm*—Patton Boggs LLP

(57) ABSTRACT

A molecular contamination monitoring system includes a piezoelectric measurement sensor exposed to a molecular constituent to be measured; a piezoelectric reference sensor; and a filter for filtering said molecular constituent, the filter located between the reference sensor and the measurement environment. The reference sensor is exposed to the same ambient conditions of temperature, pressure and humidity as the measurement sensor. Alternatively, there may be a plurality of different reference sensors having different filters, or there may be a plurality of different measurement sensors.

21 Claims, 10 Drawing Sheets

SYSTEM AND METHOD FOR MEASURING MOLECULAR ANALYTES IN A MEASUREMENT FLUID

BACKGROUND OF THE INVENTION

1. Field of the Invention

The present invention relates to real-time monitoring of chemical and physical interactions between gases and solid surfaces for purposes including detection of molecules, such as airborne molecular contaminants pertaining to manufacturing and processing environments.

2. Statement of the Problem

Many manufacturing processes and technologies are susceptible to molecular contaminants (MC) in the form of airborne or gas-phase molecular contaminants (AMC) and in the form of the related surface molecular contamination (SMC) resulting from chemical interactions between AMC and critical surfaces exposed to the same. Such critical surfaces, called "subject surfaces" herein, are, for example: integrated circuit surfaces, such as resist, silicon, and other semiconductors; wiring surfaces made of tungsten, aluminum, or other metals; silicon dioxide surfaces; optical surfaces; mechanical surfaces; surfaces of hard disks; surfaces of flat panel displays; etc. Detrimental effects of SMC include, for example, changes in the chemical, electrical, and optical qualities of critical surfaces. These detrimental effects decrease product performance and reliability and raise product costs. Some examples of such detrimental effects to the above-mentioned critical surfaces include T-topping of resist—an anomaly that undercuts line geometries and leads to device failures and yield reductions; defective epitaxial growth; unintentional doping; uneven oxide growth; changes in wafer surface properties; corrosion; and decreased metal pad adhesion. Many of these effects become particularly detrimental as line widths smaller than 0.13 microns become commonplace. Further, as wafer sizes increase and as device geometry decreases, the demand for more sensitive monitoring techniques will increase. In the optics industry, SMC is a well-known cause of hazing of optical surfaces. SMC also causes friction problems in certain mechanical devices, such as hard disk drives, since SMC-contaminated surfaces may have a significantly higher coefficient of friction than uncontaminated surfaces. SMC also affects the manufacture of hard disk drives and flat panel displays, which, for reasons known in the art, are typically carried out in a plurality of "mini" clean rooms.

The various AMCs causing detrimental SMC may be grouped into four general categories: acids, bases, condensables, and dopants, otherwise referred to as SEMI F21-95 Classes A, B, C, and D. Some AMCs, though, are of no particular class.

Sources for AMC/SMC include inadequate filtration of recirculated air; cross-process chemical contamination within a bay or across a facility, and recirculated air with inadequate ventilation; outgassing of clean-room materials, such as filters, gel sealants, and construction materials, especially new fabrics; as well as contaminants carried in and exuded by human beings, including their bodies, clothes, and their personal care products. When the fluid is outdoor "make-up" air, the sources of AMC/SMC include automobile exhaust, evapotranspiration from plants, and various industrial emissions. AMC also includes chemical compounds and vapors resulting from chemical breakdown of, and interaction between, the molecules within the AMC from the primary sources. Still other sources include various contaminants emanating from industrial equipment, such as pumps, motors, robots, and containers. Yet other sources include accidents, including chemical spills, and upsets in temperature and humidity controls.

AMC can cause yield losses even when present at concentrations as low as subparts per billion by volume ("ppbv"). Such processes therefore require an ultra-clean, well-monitored environment. Since different types of MC cause harm which may differ in kind and degree, it is helpful to identify the components of MC present in a manufacturing environment.

One existing manufacturing environment monitoring approach involves using one or more piezoelectric sensor (PZS). Piezoelectric sensors provide a signal output the frequency of which varies in response to an applied force. An accumulation of molecular contamination on the surface of a PZS effects a change in the PZS output, thereby making the PZS output indicative of a magnitude of accumulated contamination mass.

An improved PZS-based monitoring system involves using one PZS to measure contamination accumulation (the SMC sensor) and a hermetically sealed PZS as a reference sensor. The two sensors are subjected to the same temperature, but only the SMC sensor is exposed to an accumulation of SMC mass. By interpreting the difference between the two sensor outputs as a measure of molecular contamination, temperature-induced influence over PZS output is negated, thereby providing a sensor output which reflects the accumulated contamination mass without a temperature bias.

Although existing monitors have addressed measurement error due to temperature variation, they continue to suffer from error due to humidity and pressure fluctuation in the monitoring environment. Humidity and/or pressure fluctuations affect the SMC sensor but not the reference sensor because of the hermetic seal. Accordingly, a change in humidity and/or pressure will change the difference signal of the monitoring system independently of any change in the contaminant mass in contact with the SMC sensor, thereby providing misleading data regarding molecular contamination levels. Moreover, existing monitoring systems do not distinguish between the classes and types of contamination molecules, that is the constituents of the molecular accumulation. Instead, subject to the error sources discussed above, existing monitoring systems provide output values responsive to a total accumulation of mass rather than to the accumulation of individual contaminants or classes of contaminants.

SOLUTION

The present invention advances the art and overcomes the aforementioned problems by providing a molecular monitoring system including a reference sensor which is exposed to the humidity and/or pressure of a process environment, thereby enabling a difference signal which is indicative of a disparity in output between the two sensors corrected for humidity and/or pressure in addition to temperature. Different process environments may be provided including, but not limited to, a vacuum environment, an ambient air environment, and a pressurized gas flow environment. While the detection of molecular contamination on the surface of solids has been the primary motivation for development of the invention, it will be clear from the description below that the apparatus and method of the invention will be useful in sensing molecules for other purposes also.

In the preferred embodiment, a difference in the composition and/or quantity of contaminant accumulation between the measurement sensor and reference sensor is achieved by locating a filter between the process environment and the reference sensor. In this manner, the contamination mass captured in the filter substantially accounts for the difference in output between the measurement sensor and the reference sensor. Preferably, this contamination mass accumulation difference is reflected in the value of a difference signal resulting from a comparison of a measurement sensor output and a reference sensor output.

The invention provides a molecular monitoring system comprising: a piezoelectric measurement sensor exposed to a measurement environment; a piezoelectric reference sensor; a first filter located between the reference sensor and the measurement environment; and output electronics electrically connected to the measurement sensor and the reference sensor for providing an output signal characteristic of a constituent of a molecular accumulation on the measurement sensor. Either or both of the piezoelectric sensors may be a SAW sensor or a QCM sensor. The filter may be a chemical filter, a filter medium such as charcoal, activated charcoal, silicon, or a porous polymer based on 2,6-diphenyl-p-phenylene oxide, multi-sorbent filtration media. The filter may also be a chemically selective membrane such as a thin film polymeric material, expanded polytetrafluoroethylene, or a perfluorosulfonic acid polymer.

The invention also provides a method for monitoring a molecular constituent in a measurement environment, the method comprising: exposing a first piezoelectric sensor to the molecular constituent to provide a measurement sensor signal; filtering the molecular constituent from a fluid flow to provide a reference environment; exposing a second piezoelectric sensor to the reference environment to provide a reference sensor signal; and responsive to the measurement sensor signal and the reference sensor signal, providing an output characteristic of the accumulation of the consistent on the measurement sensor. The filtering may comprise removing hydrocarbons from the measurement environment, removing basic compounds from the measurement environment, removing acidic compounds from the measurement environment, or removing a semiconductor dopant from the measurement environment.

The invention further provides a method for monitoring a molecular constituent in a measurement environment, the method comprising: exposing a first piezoelectric sensor to an ambient environment including the molecular constituent to provide a measurement sensor signal, the ambient environment having ambient pressure and humidity conditions; exposing a second piezoelectric sensor to a reference environment not including the molecular constituent to provide a reference sensor signal, the reference environment including a condition selected from the ambient pressure and the ambient humidity; and responsive to the measurement sensor signal and the reference sensor signal, providing an output characteristic of the accumulation of the constituent on the measurement sensor.

In addition, the invention provides a system for monitoring molecular contamination in a measurement environment, the system comprising: a piezoelectric measurement sensor; a piezoelectric reference sensor; and output electronics electrically connected to the measurement sensor and the reference sensor for providing an output signal characteristic of a constituent of the molecular accumulation on the measurement sensor; wherein the reference sensor is exposed to an ambient condition other than temperature of the measurement environment. Preferably, the reference sensor is exposed to the humidity of the measurement environment. Alternatively, the reference sensor is exposed to the pressure of the measurement environment.

Numerous other features, objects, and advantages of the invention will become apparent from the following description when read in conjunction with the accompanying drawings.

DETAILED DESCRIPTION OF THE PREFERRED EMBODIMENT

Figure 1:
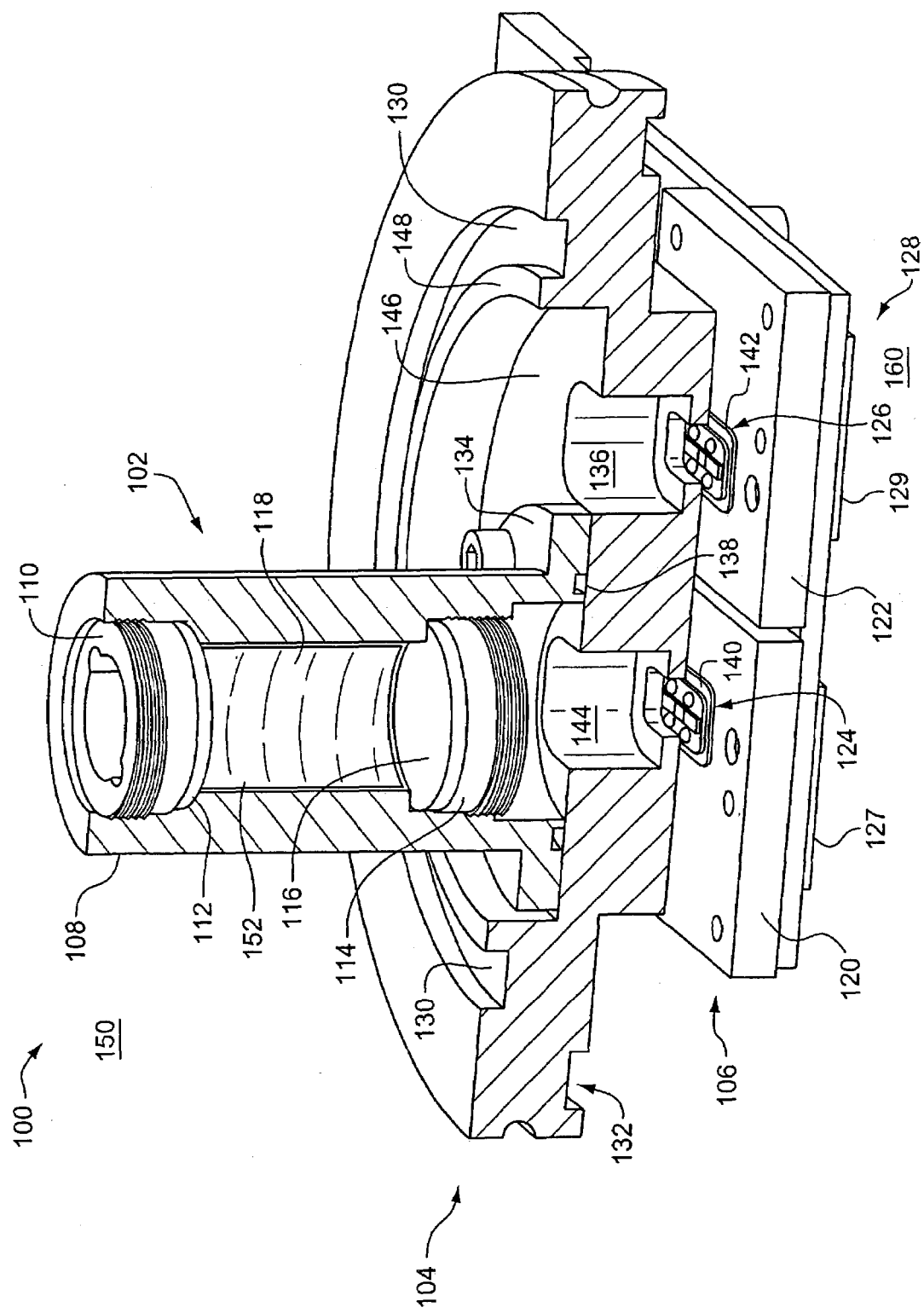
FIG. 1 is a perspective view of a portion of a molecular contamination monitoring system according to a preferred embodiment of the present invention.

FIG. 1 shows a preferred embodiment of a chemically selective molecular monitoring system 100 according to the invention. To quickly orient the reader, the system 100 includes a reference sensor 124, a measurement sensor 126, and a filter assembly 102 located between the measurement environment 150 and the reference sensor 124. The measurement sensor 126 is the sensor that is exposed to the molecular constituent that it is being measured. In this disclosure, a reference sensor is a sensor that is not exposed to the constituent being measured, but rather the constituent is filtered out.

The terms "molecule" and "molecular" are intended to restrict the invention to systems that monitor matter of a specific size range recognized in the art. That is, in non-technical language, the term "molecule" can be used loosely as being "A small particle; tiny bit". The American Heritage Dictionary of the English Language, New College Edition, Houghton Mifflin Company, Boston, 1980, page 845. This imprecise meaning is not what is meant here. On the other hand, the technical meaning of "molecule" is "The simplest structural unit that displays the characteristic physical and chemical properties of a compound." Ibid. Those skilled in the art recognize that this technical meaning of "molecule" specifies a range of sizes roughly between the size of an atom and the size of a particle, i.e., a size range centered at around a nanometer. In the art, matter that comprises molecules bound together is considered as particulate matter having a typical size of about 100 nanometers, while atoms have a typical size of 0.1 nanometers. As is normal for scientific terms, the line between atomic sizes, molecular sizes, and particulate sizes, is not sharp. For example, there is a continuous range of resistances between insulators and conductors, yet, those skilled in the art generally know what is meant by an "insulator" and what is meant by a "conductor". Likewise, in the field of matter detection, even though the line between them may not be sharp, those skilled in the art readily distinguish detection of molecular sized matter from detection of particles and the detection of atoms. Those skilled in the art recognize that significantly different technology must be used to measure contaminants or other molecular constituents in the three different size ranges.

Herein, an "SMC sensor" is a sensor that provides a signal output indicative of an accumulated mass of molecular contamination in contact with or in proximity to the SMC sensor. An SMC sensor is preferably, but need not be, a piezoelectric sensor, such as a SAW (surface acoustic wave) sensor or a quartz crystal microbalance (QCM) sensor. Herein, "measurement sensors" and "reference sensors" are preferably SMC sensors, more preferably piezoelectric sensors, and may be SAW or QCM piezoelectric sensors. A SAW monitoring system is described in U.S. patent application Ser. No. 10/178,699, entitled "Method And Apparatus For Monitoring Molecular Contamination Of Critical Surfaces Using Coated SAWs", filed Jun. 24, 2002, the disclosure of which is incorporated herein by reference.

Herein, a "measurement environment" is the environment for which a molecular constituent level is measured. The measurement environment may be a process environment in which manufacturing of integrated circuits (ICs) or other products occurs. The "process environment" may be a vacuum environment, ambient air environment, or pressurized gas flow environment, among others.

The measurement environment may also be a non-process environment including a vacuum environment, an ambient air environment, or other fluid environment. Where the measurement environment is a fluid environment, the fluid concerned may be in or emerging from a stored fluid source. Moreover, this fluid environment may be flowing or may be substantially stagnant.

"Vacuum environments" are environments at pressure reduced below atmospheric pressure. Ambient conditions, including temperature, finite pressure levels, and finite water vapor levels (and therefore finite humidity), are generally measurable in a vacuum environment. The term "fluid" is defined herein as a liquid or gas, or a vapor mixture, including air, elemental gases such as nitrogen and argon, and mixtures of the same. When an exemplary operation is described, the particular fluid used for the description is not, unless otherwise stated or clear from the context, intended as a limitation on the scope or operation of the invention. Herein, "ambient conditions" preferably include temperature, pressure, and humidity.

Figure 2:
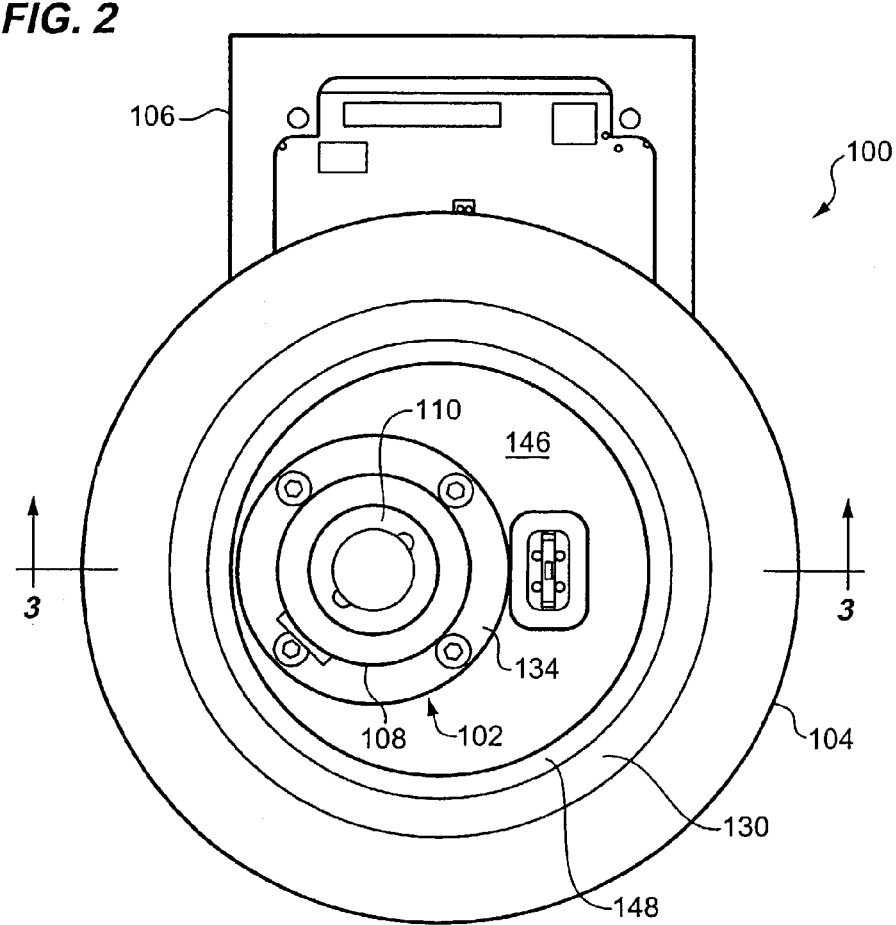
FIG. 2 is a top plane view of the monitoring system of FIG. 1.
Figure 3:
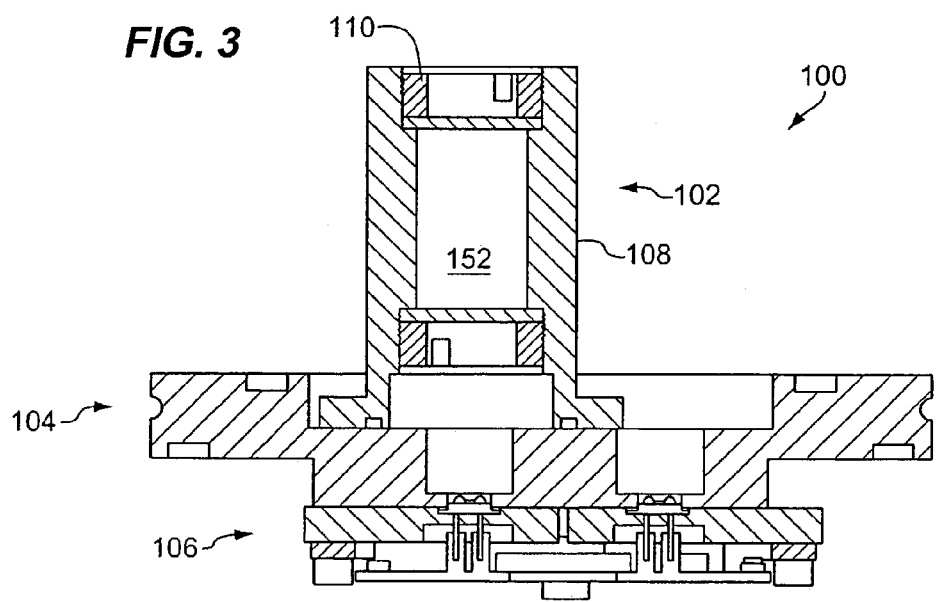
FIG. 3 is a side sectional view of the monitoring system of FIG. 1.

FIG. 1 is a perspective view of a chemically selective monitoring system 100 according to a preferred embodiment of the present invention; FIG. 2 is a top plane view of monitoring system 100 of FIG. 1; and FIG. 3 is a side sectional view of monitoring system 100 of FIG. 1. The dimensions identified in the figures of the instant application are preferred and are not intended to be limiting. In all cases, dimensions other than those indicated in the figures may be employed and all such variations are intended to be within the scope of the present invention.

Reference is made to FIGS. 1-3 in the following. Monitoring system 100 preferably includes filter 102, vacuum flange 104, and sensor platform 106. Measurement environment 150, which is preferably a process environment, typically surrounds monitoring system 100. In the preferred embodiment, filter 102 is located above vacuum flange 104. Filter 102 preferably includes filter tube 108, filter medium 118 located within filter tube 108, and attachment flange 134. Filter 102 preferably further includes retaining barriers 112 and 116, which are preferably sintered frits, and threaded end plugs 110 and 114. Filter 102 and filter medium 118 preferably both have cylindrical cross-sectional geometries, although other geometries may be employed. Filter medium 118 is preferably bounded on a first end of filter tube 108 by retaining barrier 112, which is held in place by threaded end plug 110. Similarly, filter medium 118 is preferably bounded on a second end of filter tube 108 by retaining barrier 116 and threaded end plug 114. On both ends of filter tube 108, threaded end plugs 110 and 114 are positioned to hold retaining barriers 112 and 116 and filter medium 118 in place. Retaining barriers 112 and 116 preferably prevent particles from filter medium 118 from emerging from filter 102.

Filter tube 108 is preferably made of aluminum, although other materials may be employed. Similarly, attachment flange 134, which is preferably an extension of filter tube 108, is also preferably made of aluminum. Filter tube 108 preferably extends about 1.70 inches above the upper surface of vacuum flange 104, although other dimensions may be employed. Filter tube 108 preferably has an outside diameter of about 1.15 inches and preferably has walls which are about 0.265 inches thick. However, other dimensions maybe provided for filter tube 108. Filter cavity 152 is preferably about 1.00 inch tall and about 0.62 inches wide, although other dimensions may be used.

Preferably, threaded end plugs 114 and 116 are made of aluminum, although other materials may be employed. Retaining barriers 112 and 116 are preferably sintered frits made of stainless steel having a 5-micron porosity. However, porosities ranging from 40 microns to 100 microns may also be employed. Moreover, materials other than stainless steel may be used for retaining barriers 112 and 116. Filter medium 118 may be made of Tenax® GC, (a porous polymer based on 2,6-diphenyl-p-phenylene oxide), silicon, chemically doped versions of Tenax® GC and/or silicon, and/or other commercially available filtration media. Filter medium 118 may be made of single or multi-sorbent filtration media.

Vacuum flange 104 is preferably located between filter 102 and sensor platform 106. Seal 138 is preferably located between filter 102 and vacuum flange 104. Seal 138 may be made of Teflon® (polytetrafluoroethylene) or Teflon-encapsulated rubber, other elastomers, such as FKM, or other suitable sealant. Circumferential chamber 146 is preferably centered with respect to vacuum flange 104 and preferably serves to house filter 102, reference sensor cavity 144, and measurement sensor cavity 136. Chamber 146 preferably has a diameter of 2.55 inches. However, other dimensions may be used. Ridge 148 is immediately radially outward of chamber 146. Ridge 148 is preferably 0.125 inches wide, thereby providing an outside diameter of 2.80 inches. However, other dimensions may be provided for ridge 148. Groove 130 preferably houses an o-ring seal (not shown) and is preferably about 0.235 inches wide, thereby providing an outside diameter of 3.27 inches. However, other dimensions may be employed for groove 130. Clamping groove 132 preferably extends about the circumference of vacuum flange 104 close to the outside edge. The outside diameter of vacuum flange 104 is preferably about 4.33 inches. However, smaller or larger diameters may be employed for vacuum flange 104.

In the preferred embodiment, reference sensor cavity 144 is located below filter 102 and extends most of the way to sensor platform 106. Similarly, measurement sensor cavity 136 is preferably arranged substantially parallel to reference sensor cavity 144 and also extends down most of the way to sensor platform 106. Each sensor cavity preferably has a width of about 0.48 inches and a height of about 0.38 inches, although other dimensions may be employed for sensor cavities 144 and 136.

In the preferred embodiment, sensor platform 106 includes reference sensor retainer base 120, reference sensor seal 140, measurement sensor retainer base 122, measurement sensor seal 142, and output electronics assembly 128.

In the preferred embodiment, reference sensor 124 and measurement sensor 126 are located at the bottom of reference sensor cavity 144 and measurement sensor cavity 136, respectively, and are exposed to measurement environment 150, though reference sensor 124 is exposed through filter 102. Preferably, seals 140 and 142 are located below sensors 124 and 126, respectively, and isolate ambient environment 160, which includes sensor platform 106 and output electronics assembly 128, from measurement environment 150. Preferably, reference sensor retainer base 120, which is preferably made of aluminum, underlies reference sensor seal 140. Likewise, reference sensor retainer base 122, also preferably made of aluminum, preferably underlies measurement sensor seal 142. Output electronics assembly 128 preferably includes portions 127 and 129 and is preferably located below sensor retainer bases 120 and 122.

It will be appreciated that the following discussion of the details of reference sensor 124 and reference sensor seal 140 applies equally to measurement sensor 126 and measurement sensor seal 142. The discussion is limited to reference sensor 124 and reference sensor seal 140 for the sake of brevity. In the preferred embodiment, reference sensor 124 is about 0.518 inches long, about 0.24 inches wide, and about 0.60 inches thick, although other dimensions may be used. Reference sensor seal 140 is preferably about 0.613 inches long, about 0.335 inches wide, and about 0.020 inches thick, although other dimensions may be used. Reference sensor seal 140 is preferably made of polytetrafluoroethylene, but other materials may be used. Sensors 124 and 126 are preferably SMC sensors, more preferably piezoelectric sensors, and may be QCM or SAW sensors.

Figure 4:
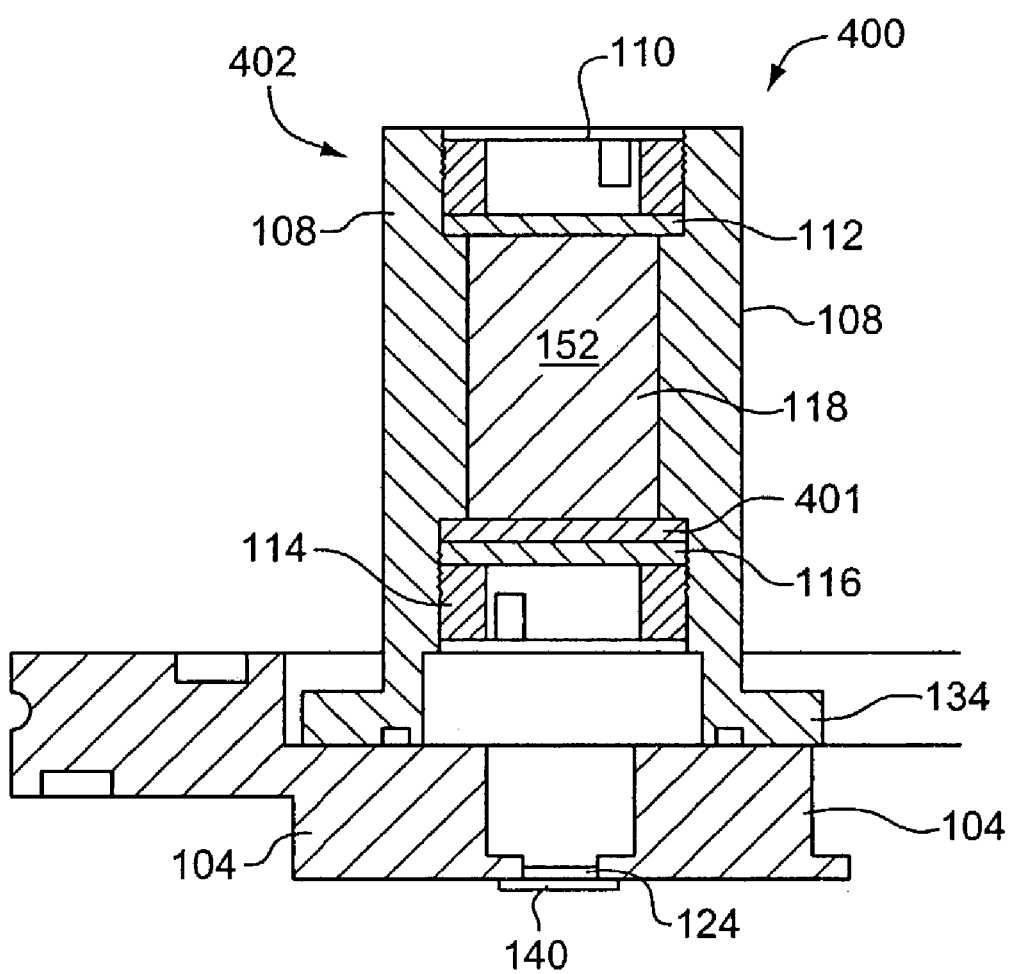
FIG. 4 is a side sectional view of a portion of an alternative embodiment of the monitoring system of FIG. 1.

FIG. 4 is a side sectional view of a portion of an alternative embodiment of a monitoring system 400 including filter 402 above vacuum flange 104. The embodiment of FIG. 4 is the same as that of the embodiment 100 of FIGS. 1-3 except that chemically selective membrane 401 is deployed below filter medium 118 within filter 402. However, it will be appreciated that chemically selective membrane 401 could be deployed within filter 402 in the absence of filter medium 118. In a preferred embodiment, chemically selective membrane 401 is a thin film, typically polymeric material. However, other materials may be used including Nafion® (perfluorosulfonic acid polymer) or other ion-exchange membrane, Gortex®, and/or other permeable polymer films which allow only certain types of molecules to pass therethrough. Optionally, chemically selective membrane 401 could be a membrane described in U.S. application Ser. No. 10/178,818, entitled "Molecular Contamination Monitoring System And Method", filed Jun. 24, 2002, the disclosure of which is incorporated herein by reference.

In a preferred embodiment, chemically selective membrane 401 is about 0.125 inches thick. The diameter of chemically selective membrane 401 can be selected to substantially match the internal diameter of filter cavity 152. Where deployed within filter cavity 152, chemically selective membrane 401 could be located anywhere along the length of filter cavity 152, as long as an appropriate seal is formed between chemically selective membrane 401 and the internal wall of filter cavity 152.

Figure 5:
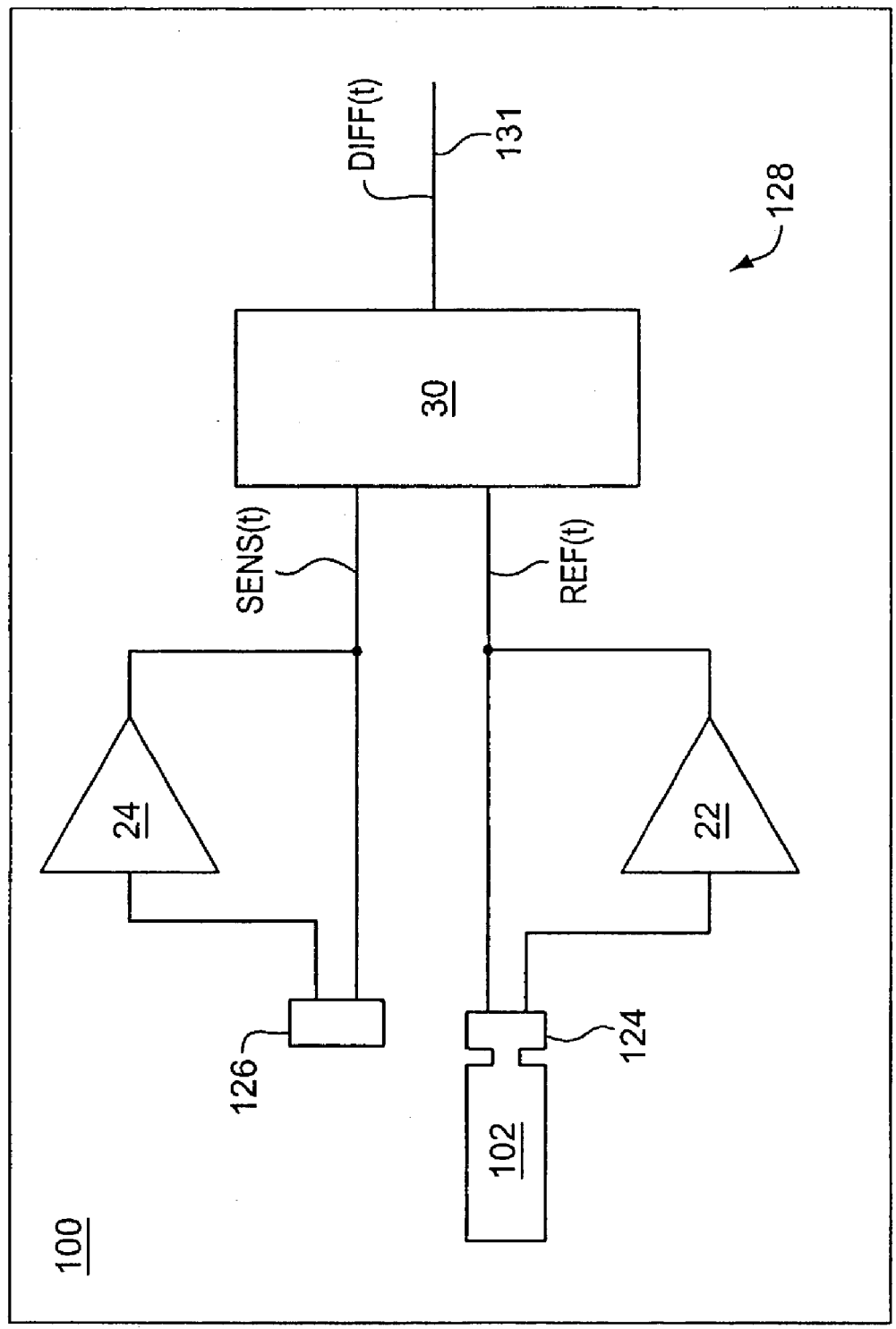
FIG. 5 is a schematic view of a portion of the electronics assembly of FIG. 1 for providing a difference signal from the reference sensor and the measurement sensor of FIG. 1 according to a preferred embodiment of the present invention.

FIG. 5 is a schematic view of a portion of output electronics assembly 128 for providing a output signal on output 131 indicative of the molecular constituents on measurement sensor 126. In the preferred embodiment, the output signal is a difference signal DIFF(t) indicative of the difference in the signals from reference sensor 124 and measurement sensor 126. The FIG. 5 circuit comprises an oscillator circuit formed by connecting output leads from sensors 124 and 126 to amplifiers 22 and 24, respectively, in a manner known in the art. Amplifiers 22 and 24 may include phase-shifting elements to provide desired oscillation characteristics, as is also known in the art. The oscillating frequencies depend, in part, on the acoustic wave propagation velocities. The change in acoustic wave propagation velocities, caused by increased mass on the surfaces of sensors 124 and 126 due to molecules interacting with the surfaces, therefore changes the oscillating frequencies.

Output electronics assembly 128 preferably includes comparator 30 which receives oscillating signal SENS(t) from measurement sensor 126 via amplifier 24 and oscillating signal REF(t) from reference sensor 124 via amplifier 22 and generates difference signal DIFF(t) representing the difference between the SENS(t) and REF(t) frequencies. This frequency difference is commonly referred to as a "beat frequency". The value of the DIFF(t) frequency preferably corresponds to the disparity between the accumulation of mass on measurement sensor 126 over that on reference sensor 124. This frequency is preferably on the order of half a megahertz (MHz), ranging typically from 0.3 MHz to 0.8 MHz.

Although measurement sensor 126 and reference sensor 124 are preferably SAWs in the embodiment of FIG. 5, it will be appreciated that sensors 124 and 126 could be other types of SMC sensors, including, but not limited to, various types of piezoelectric sensors. SAW detector circuits are described in U.S. Pat. No. 6,122,954 issued Sep. 26, 2000 to William D. Bowers and U.S. Pat. No. 4,871,984 issued Oct. 3, 1989 to Laton et al., both of which are hereby incorporated by reference as though fully disclosed herein.

As known in the art, the output signal DIFF(t) is processed by electronics to provide an output characteristic of the constituents of the molecular accumulation on measurement sensor 126. The output signal may be processed by a computer or other processing system to provide output information that may be in the form of a display, a printed output such as a graph, audio, or other output.

Figure 6:
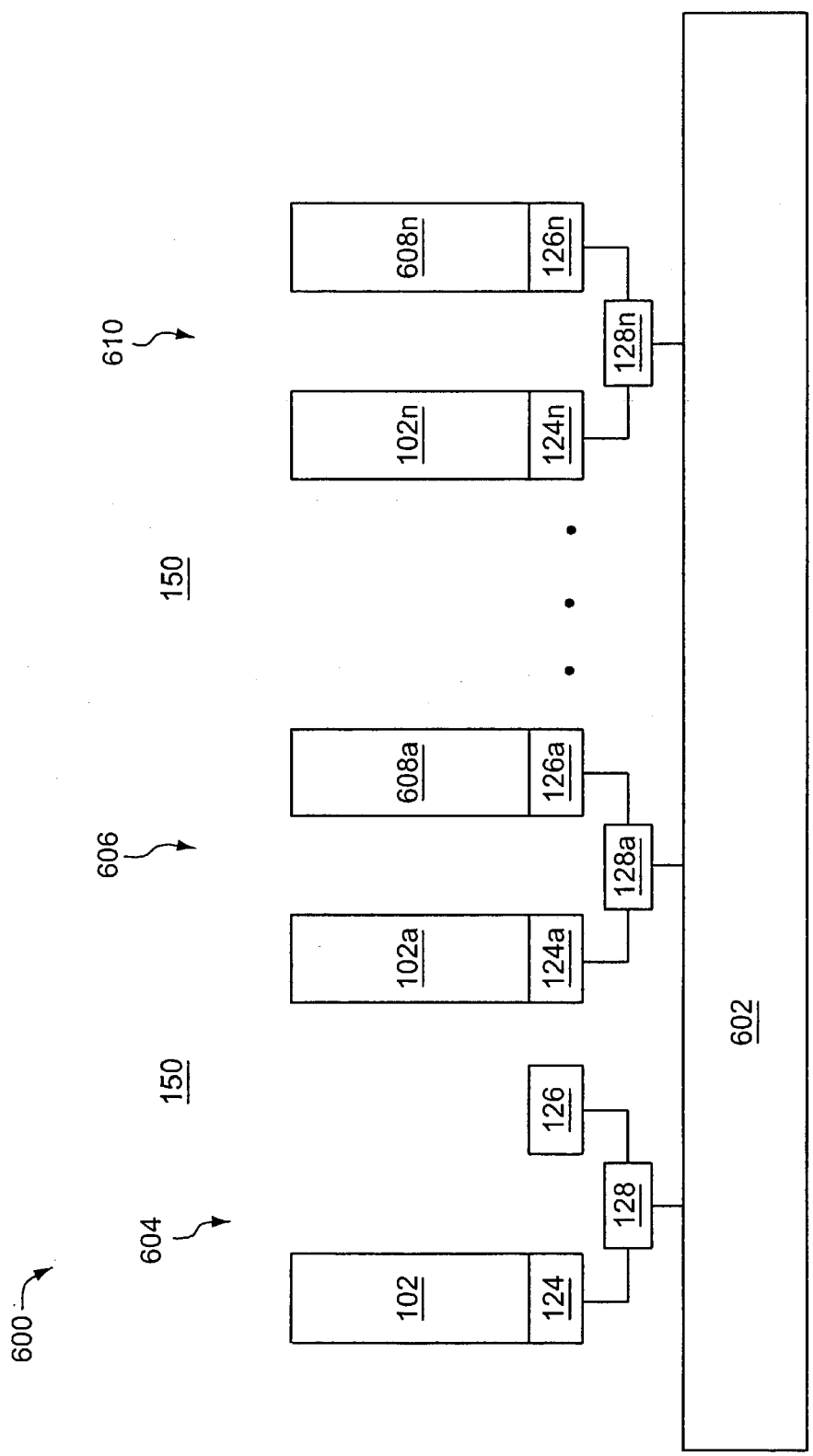
FIG. 6 is block diagram of a monitoring system according to an alternative embodiment of the present invention.

FIG. 6 is a block diagram of a monitoring system 600 according to an alternative embodiment of the present invention. Monitoring system 600 preferably includes sensor pairs 604, 606, and 610. It will be appreciated that any number of additional sensor pairs could be added to the embodiment of FIG. 6. At left, sensor pair 604 includes reference sensor 124 having filter 102 located in between sensor 124 and measurement environment 150, which is preferably a vacuum environment. Sensor pair 604 also preferably includes measurement sensor 126 and output electronics assembly 128, which is preferably coupled to both reference sensor 124 and measurement sensor 126. Output electronics assembly 128 preferably provides contamination measurement data for sensor pair 604 to output data processor 602. Output data processor 602 may include a signal analyzer, a computer, a display, a printer, or other processing electronics as known in the art.

Sensor pair 606 preferably includes filter 102a, reference sensor 124a, which is preferably separated from measurement environment 150 by filter 102a, measurement sensor 126a, and output electronics assembly 128a, which is preferably coupled to both reference sensor 124a and measurement sensor 126a. Output electronics assembly 128a is preferably coupled to output data processor 602. Parts of sensor pair 606 are preferably arranged much as the similarly numbered parts are in sensor pair 604. An additional feature of sensor pair 606 is the addition of filter 608a, which is preferably separates measurement sensor 126a from measurement environment 150. Filter 608a is used to filter out a constituent that may interfere with the measurement of the particular constituent that is desired to be measured. Filter 608a does not filter out the constituent that it is desired to measure.

Sensor pair 610 includes reference sensor 124n, filter 102n, measurement sensor 126n, filter 608n, and output electronics assembly 128n, which assembly is coupled to output data processor 602. The arrangement of the components of, sensor pair 610 is preferably the same as that of the similarly numbered parts of sensor pair 606.

Figure 7:
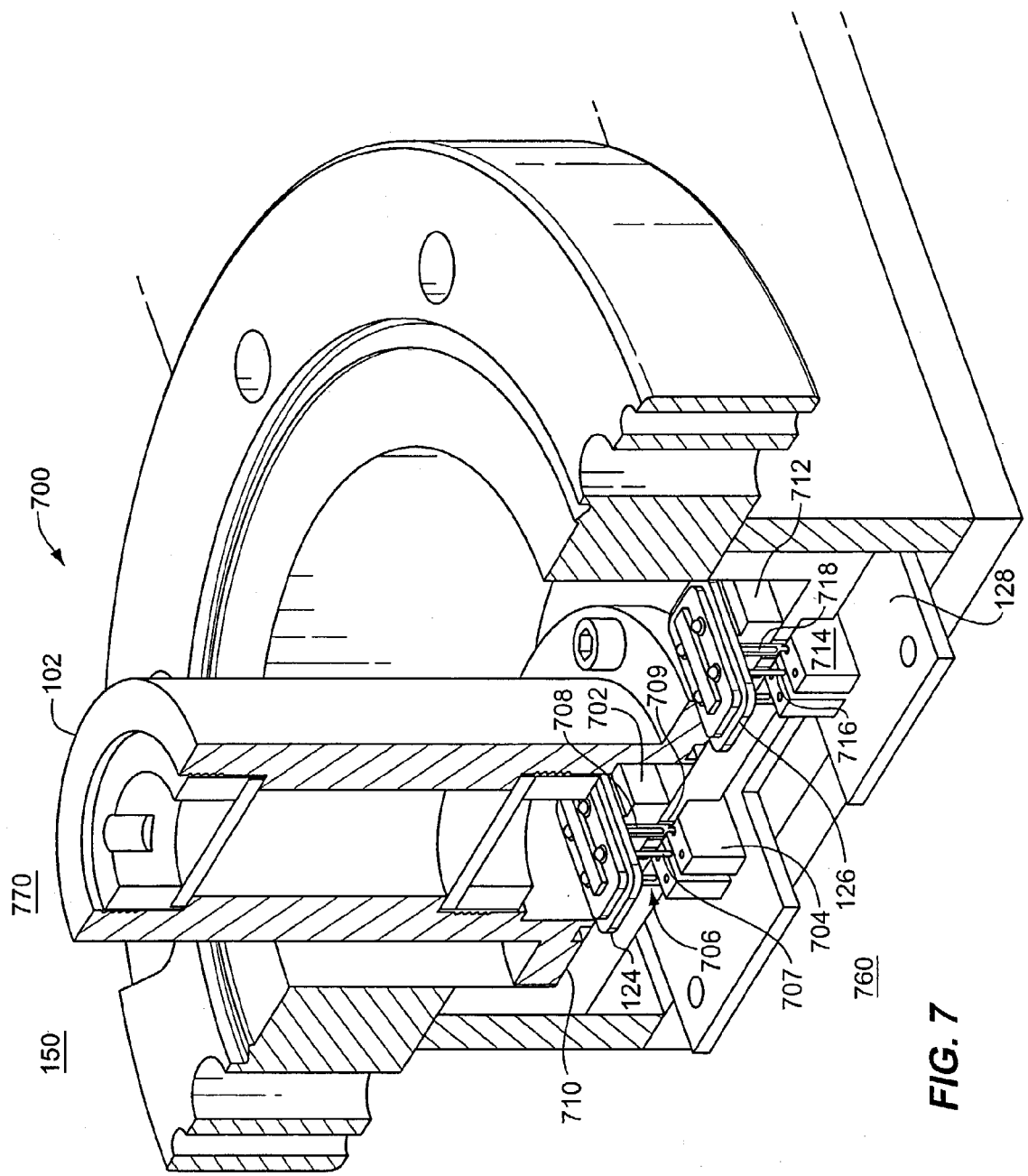
FIG. 7 is a perspective view of a molecular contamination monitoring system according to an alternative embodiment of the present invention.

FIG. 7 is a perspective view of a molecular contamination monitoring system 700 according to an alternative embodiment of the present invention. Monitoring system 700 includes many features in common with monitoring system 100, such as filter 102. Accordingly, this discussion is directed to the differences between monitoring system 100 and monitoring system 700.

In the embodiment of FIG. 1, Teflon® (polytetrafluoroethylene) seals 140 and 142 are located below sensors 124 and 126, respectively, to separate measurement environment 150, which is preferably a vacuum environment, from the ambient air environment 160 below sensors 124 and 126. In contrast, in the embodiment of FIG. 7, the seal between the measurement environment 150 and the ambient environment 760 is made by glass seals 709 through which the sensor electrical connectors 706 pass. The design of FIG. 7 isolates the stresses resulting from making the seal from the sensor 124 and 126 themselves. These stresses can cause the sensors to take significant time, such as days, to settle down after the seal is closed, if the stresses are applied more directly to the sensor.

Turning to the details of the embodiment of FIG. 7, reference sensor 124 is located on sensor support 702, which positions sensor 124 substantially above interface 710 between measurement environment 150 and ambient air environment 760 on the opposite side of interface 710. Electrical connectors 706 preferably comprise two parts, sensor wires 707 and sensor wire sleeves 708. Sleeves 708 form a socket into which wires 707 fit tightly. Sensor support 702 may be made of Teflon® and serves as an electrical insulator between each of sensor wire sleeves 708 and between sensor wire sleeves and reference sensor 124. It is constructed such that the height of sensor support 702 is greater than the effective height of sensor wire sleeves and thereby prevents the base of reference sensor 124 from coming into contact with sensor wire sleeves 708. Preferably, sensor wires 707 lead from reference sensor 124 to sensor wire sleeves 708. Sensor wire sleeves 708 lead from sensor wires 707 to reference sensor wire housing 704. Glass seals 709 surround sensor wire sleeves 708 and are fused to interface 710 and provide highly effective separation of the ambient air environment 760 of electronics assembly 706 and measurement environment 150. The isolation of the portion of the system that is gripped by the glass seals 709, i.e., the sleeves 708, and the sensors 124 and 126, prevents the stresses caused by the seal from affecting the sensors. The configuration of sensor wires 716, sensor wire sleeves 718, sensor support 712, and sensor wire housing 714 with respect to measurement sensor 126 is preferably the same as described above in connection with reference sensor 124.

The generation of difference signals indicative of a disparity in contaminant mass accumulation between reference sensor 124 and measurement sensor 126 preferably occurs the same way in monitoring system 700 as in monitoring system 100. Accordingly, that discussion is not repeated in this section or in the discussion of operation presented later in this document.

Figure 8:
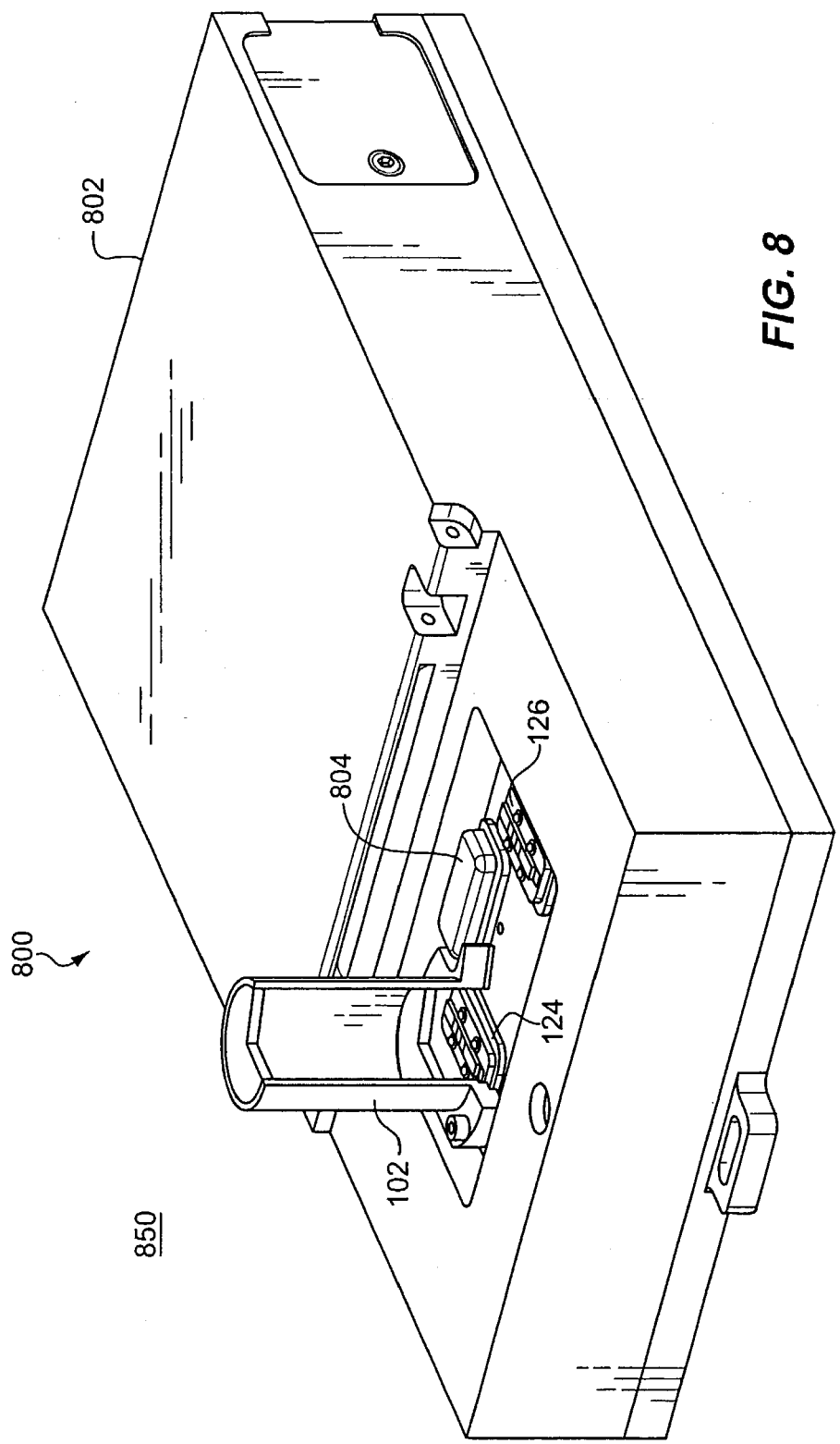
FIG. 8 is a perspective view of a molecular contamination monitoring system for operation in an ambient air environment according to a preferred embodiment of the present invention.

FIG. 8 is a perspective view of a molecular contamination monitoring system 800 for operation in measurement environment 850 according to a preferred embodiment of the present invention. In the embodiment of FIG. 8, measurement environment 850 is preferably an ambient air environment. Accordingly, in this embodiment, there is preferably no need to protect wires and electronic equipment from measurement environment 850. This situation preferably simplifies the design of monitoring system 800 in comparison with the monitoring system of FIG. 1.

In this embodiment, filter 102 is located between measurement environment 850 and reference sensor 124. For the sake of simplicity, no filter medium is shown in FIG. 8. However, the same choices for the material for a filter medium are available in the embodiment of FIG. 8 as were discussed in connection with filter medium 118 of FIGS. 1 and 4.

Output electronics assembly 128 is preferably enclosed within electronics housing 802. A thermistor 804 is used for taking temperature data. The generation of difference signals indicative of a disparity in contaminant mass accumulation between reference sensor 124 and measurement sensor 126 preferably occurs the same way in monitoring system 800 as in monitoring system 100. Accordingly, that discussion is not repeated in this section or in the description of operation later in this document.

Figure 9:
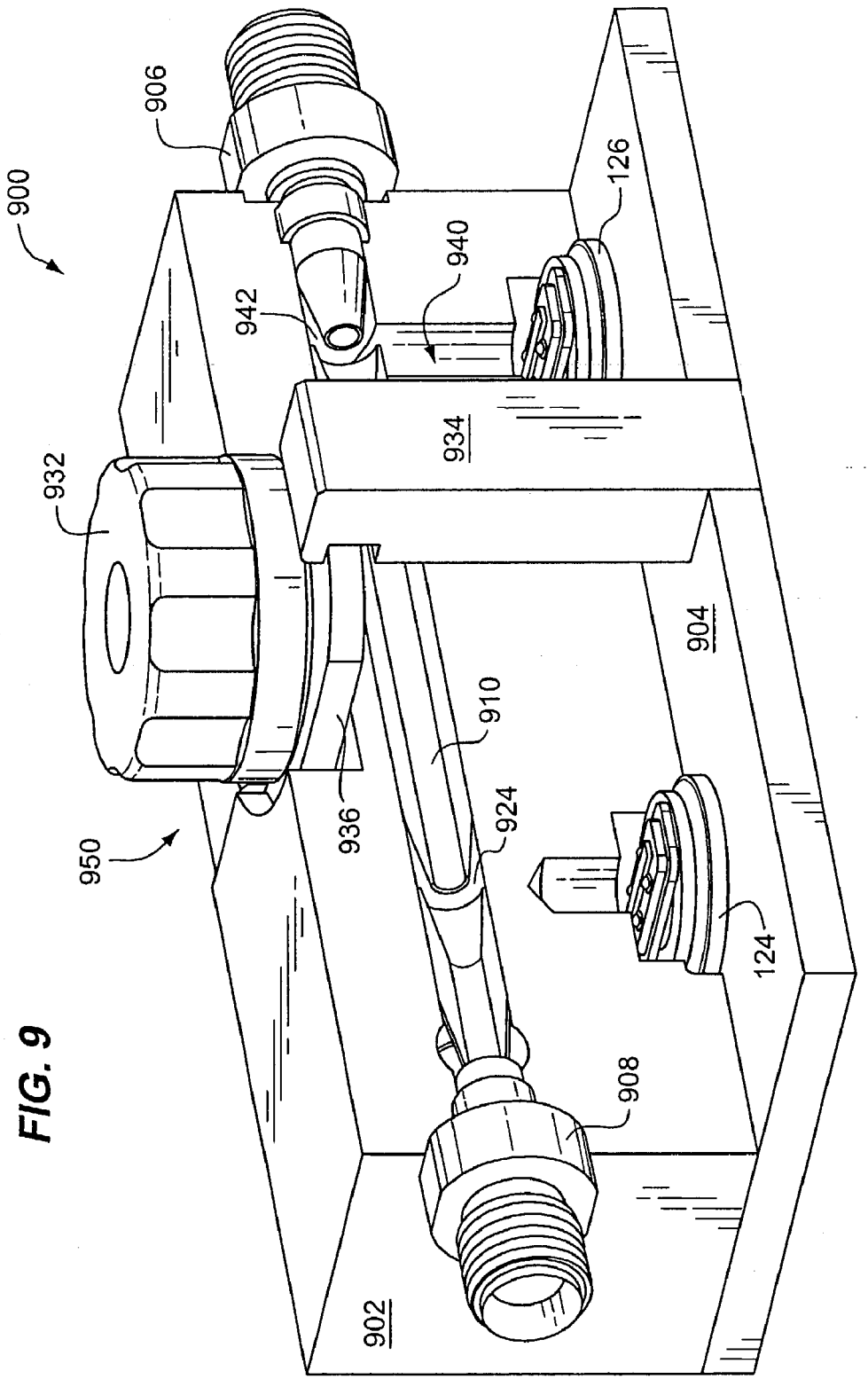
FIG. 9 is a perspective view of a molecular contamination monitoring system for operation in a flowing or pressurized gas environment according to a preferred embodiment of the present invention.

FIG. 9 is a perspective view of a molecular contamination monitoring system 900 for operation in a flowing or pressurized gas environment according to a preferred embodiment of the present invention. Preferably, pressure head 902 is located adjacent to assembly base 904. Pressure head 902 preferably includes gas inlet fitting 906, gas outlet fitting 908, and tubing 910 between fittings 906 and 908. Preferably, gaps 942 and 924 are present between tubing 910 and fittings 906 and 908 to permit diffusion of gas flowing from inlet 906 to outlet 908 to measurement sensor 126 and reference sensor 124, respectively. A third gap 952 (FIG. 10) permits diffusion to a temperature and relative humidity senor 938. Preferably, diffusion channel 940 leads from gap 942 to measurement sensor 126. Diffusion of gas via gap 924 is discussed in connection with FIG. 10.

Assembly base 904 preferably supports reference sensor 124 at left and measurement sensor 126 at right. Assembly base 904 is preferably rigidly attached to post 934. In this embodiment, rotating knob 932 engages threaded rotor 936. Rotor 936 rotates with knob 932 to engage and release latch assembly 950 from post 934. Rotor 936 preferably transmits the tightening force of knob 932 to post 934, and by extension, to base 904. In this manner, rotation of knob 932 to a suitable level of torque preferably effects a gas-tight seal between base 904 and pressure head 902.

Figure 10:
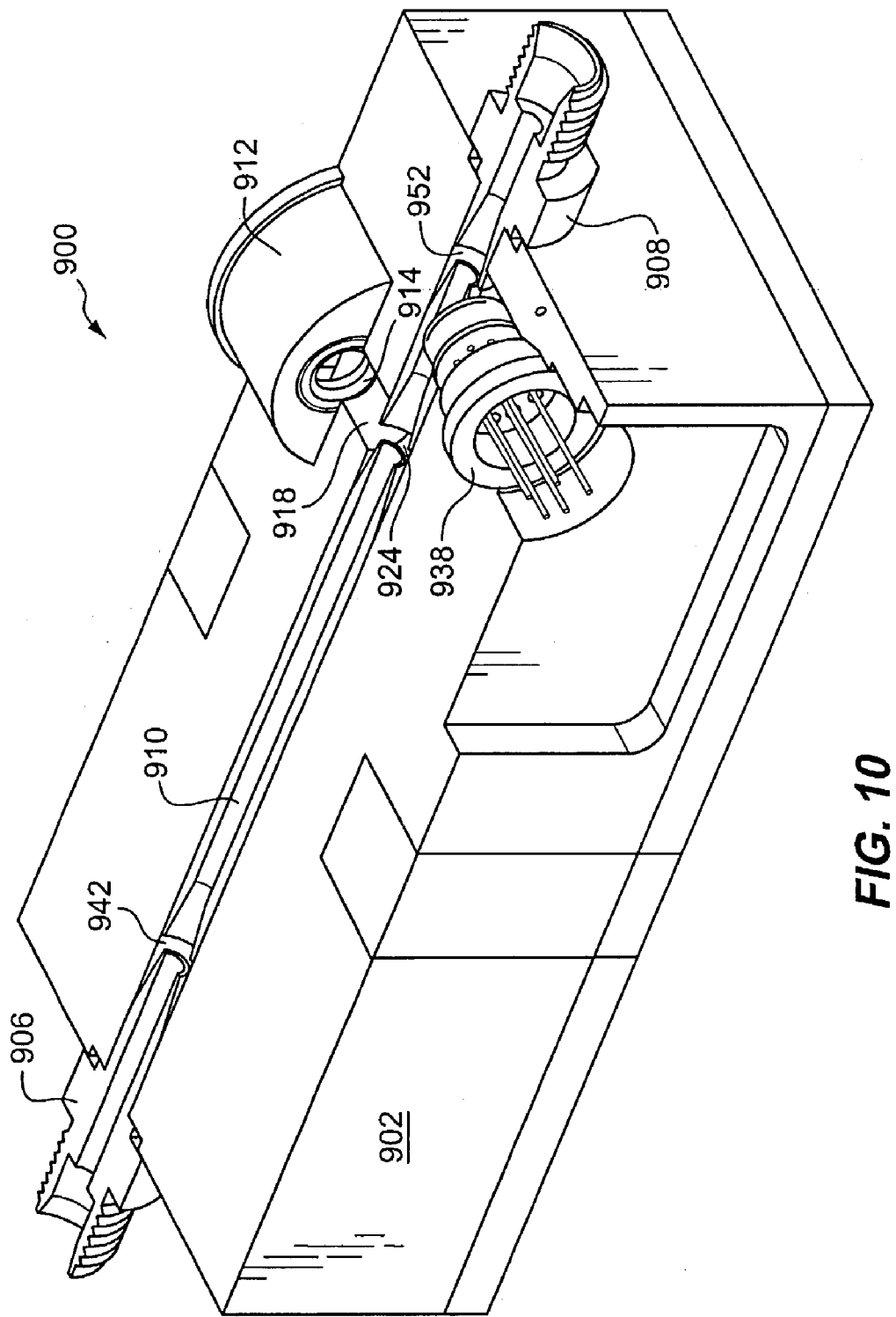
FIG. 10 is another perspective view of the monitoring system of FIG. 9.

FIG. 10 is another perspective view of the monitoring system of FIG. 9. In this embodiment, it is seen that gap 924 in gas tubing 910 is preferably adjacent to filter inlet channel 918. Filter inlet channel 918 preferably leads from gap 924 to filter inlet 914 of filter 912. Preferably, temperature and relative humidity sensor assembly 938 is located either near or adjacent to tubing 910. Gap 952 permits diffusion of the gas flowing from inlet 906 to outlet 908 to sensor assembly 938.

Figure 11:
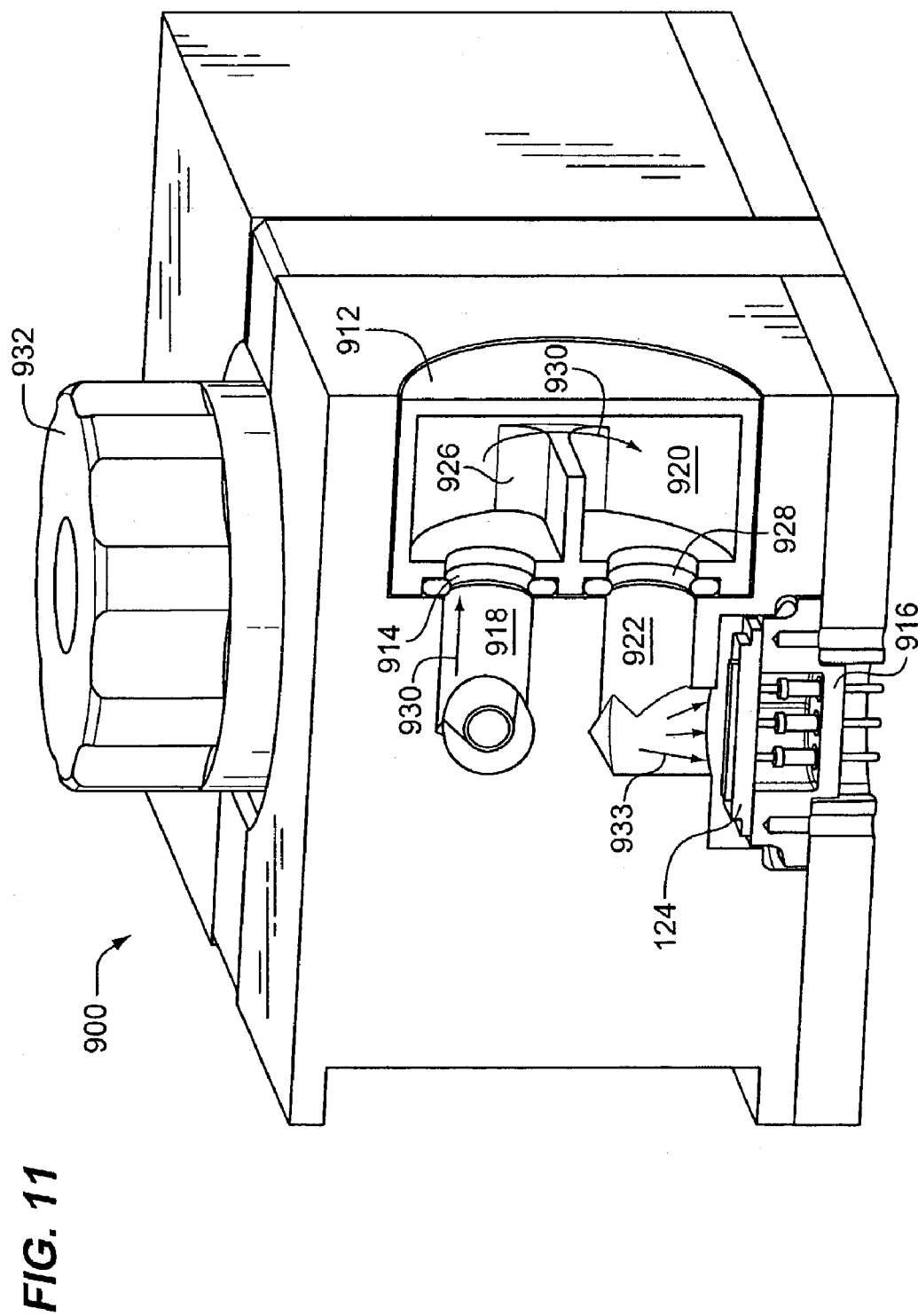
FIG. 11 is a partial sectional view of the monitoring system of FIG. 9.

FIG. 11 is a partial sectional view of monitoring system 900 of FIG. 9. Preferably, filter inlet channel 918 leads to filter inlet 914 to filter 912. Filter chamber 920 contains a filter medium. A baffle 926 within filter chamber 920 preferably forces the gas to take a longer flow path through the filter medium. Filter outlet channel 922 preferably leads from filter outlet 928 connecting to filter 912 to the top of reference sensor 124. Electronic connectors 916 connect reference sensor 124 to sensor electronics (not shown in FIG. 11). The filter medium for filter 912 may be selected from the same materials available for filter 102 of monitoring systems 100, 400 discussed in connection with FIGS. 1 and 4. Thus, the gas diffusing from diffuser gap 924 (FIG. 9) follows a flow path 930 through filter 912 to reference sensor 124.

The diffusion of gas to reference sensor 124 is filtered and the diffusion of gas to measurement sensor 126 is not. Accordingly, a difference signal indicative of a disparity between contaminant mass accumulation at reference sensor 124 and measurement sensor 126 is preferably determined by the contaminant mass accumulation within filter 912. The generation of this difference signal occurs in the same manner as described in connection with monitoring system 100 of FIG. 1 elsewhere herein. Accordingly, that discussion is not repeated in this section or in the discussion of operation below.

The construction and operation of flow diffusion systems such as shown in FIGS. 9-11 is disclosed in great detail in U.S. patent application Ser. No. 10/178,818, filed Jun. 24, 2002, which is hereby incorporated by reference as though fully disclosed herein.

The operation of monitoring system 100 is now discussed with reference to FIGS. 1-6. In the preferred embodiment, monitoring system 100 is disposed within measurement environment 150. In the preferred embodiment, sensors measure molecular contamination in measurement environment 150 by measuring accumulation of contaminant mass at sensor surfaces. Preferably, molecular contaminants migrate in various directions throughout measurement environment 150 on an ongoing basis. Accordingly, some proportion of this ongoing migration proceeds toward measurement sensor 126 and some proportion through filter 102 toward reference sensor 124. The migrated molecular contaminants preferably interact with the surfaces of reference sensor 124 and measurement sensor 126 causing an accumulation of contamination mass at the sensor surfaces. The signal outputs from various types of sensors preferably change in response to increasing amounts of accumulated mass according to principles which are known in the art, thereby permitting conclusions to be drawn about the prevailing levels of surface molecular contamination and airborne molecular contamination in measurement environment 150.

In the preferred environment, both reference sensor 124 and measurement sensor 126 are equally exposed to the ambient conditions, including temperature, humidity, and pressure, of measurement environment 150. Therefore, a disparity in the signal outputs of sensors 124 and 126 is preferably due purely to a disparity in contaminant mass accumulation at these sensors.

In the preferred embodiment, molecular contamination in measurement environment 150 diffuses toward measurement sensor 126 and toward filter 102, which filter is preferably located between measurement environment 150 and reference sensor 124. Accordingly, measurement sensor 126 preferably receives an accumulation of contaminant mass generating an output signal, SENS(t) (FIG. 5), indicative of this accumulation. In one embodiment, filter 102 preferably prevents substantially all molecular contamination from reaching reference sensor 124. In this embodiment, the difference between the frequencies of SENS(t) and REF(t), represented by the signal DIFF(t), is preferably indicative of the total accumulated contaminant mass on measurement sensor 126 with little if any error being introduced by variation in the ambient conditions.

In the preferred embodiment, the exposure of reference sensor 124 to ambient conditions including pressure and humidity reduces the error in contaminant measurement data due to pressure fluctuations by a factor of about three hundred in comparison with existing monitoring systems having hermetically sealed reference sensors. Similarly, the exposure of reference sensor 124 to humidity preferably reduces contaminant measurement data dependence on humidity fluctuations by a factor of ten, for silicon dioxide sensor crystal surfaces, in comparison with existing monitoring systems having humidity-insulated reference sensors.

In an alternative embodiment, instead of blocking substantially all molecular contaminants with filter 102, a chemically selective filtering process may be employed. Specifically, filter medium 118 and/or chemically selective membrane 401 may be deployed to block a selection of contaminants and to let others pass through to reference sensor 124. This approach would enable monitoring system 100 to measure contaminants falling into selected chemical categories and even individual selected chemical compounds.

Preferably, contaminants which are blocked by filter 102 are what will be measured by monitoring system 100. For example, an activated charcoal filter medium 118 preferably traps hydrocarbons in filter 102. Accordingly, contaminants other than hydrocarbons would preferably reach reference sensor 124. As with previously discussed embodiments, all contaminants would preferably reach measurement sensor 126. Accordingly, in this embodiment, the resulting DIFF(t) signal is preferably indicative of an accumulation of hydrocarbon contamination alone.

In another embodiment, monitoring system 100 may be configured to distinguish between organic and inorganic compounds. Specifically, deploying a filter medium 118 and/or membrane 401 which traps only organic materials, i.e., hydrocarbons, would effectively cause monitoring system 100 to measure the accumulation of organic compounds on measurement sensor 126. The same principle may be applied to acids, bases, or semiconductor dopants. Semiconductor dopants are elements used in doping semiconductors in the integrated circuit industry, such as boron and phosphorus. Moreover, by configuring filter medium 118 to trap only one chemical out of many sources of contamination, monitoring system 100 could be configured to monitor trace levels of contamination of the filtered chemical in an environment containing high concentrations of other types of contamination.

In another alternative embodiment, filters may be deployed over measurement sensor 126 as well as reference sensor 124. Moreover, different blends of filtration medium 118 could be deployed within each of the filters.

FIG. 6 is block diagram of a monitoring system 600 according to an alternative embodiment of the present invention. In this embodiment, a plurality of sensor pairs 604, 606, and 610 are preferably deployed, with each sensor pair including one measurement sensor and one reference sensor. Each sensor pair may be configured to measure a different contaminant or different group of contaminants. The selection among these options may be implemented by appropriately selecting the characteristics of the filters above each of the sensors.

Optionally, a plurality of sensor pairs may be employed to obtain a variety of measurements identifying molecular contamination in greater detail than would be possible with a single sensor pair. For example, in the embodiment of FIG. 6, sensor pair 604 is preferably employed to measure a mass accumulation of all contaminants within measurement environment 150. Sensor pairs 606, 610, and others, if deployed, could be used to measure specific groups of contaminants and/or specific contaminants. As another alternative, reference sensors 102a through 102n can be eliminated, and a single filtered reference sensor can be used in combination with a plurality of measurement sensors. This simpler arrangement permits one filtered sensor to provide a reference for several measurement sensors. The different measurement sensors may have different sensing surfaces or coatings as described in U.S. patent application Ser. No. 10/178,699 filed Jun. 24, 2002, which is hereby incorporated by reference as though fully disclosed herein. As another alternative, a plurality of filtered reference sensors can be combined with a single measurement sensor.

For example, monitoring system 600 could be configured to separately measure the organic and inorganic components of the total molecular contamination. In pursuit of this objective, sensor 102 of sensor pair 604 would preferably include a filter medium which filters out organic material. Accordingly, a difference signal emerging from sensor pair 604 would preferably be indicative of accumulated organic molecular contamination at measurement sensor 126.

Likewise, sensor pair 606 could be configured to measure inorganic material. In this embodiment, sensor 102a preferably includes a filter medium which filters out inorganic material. Filter 608a is preferably omitted in this embodiment. Accordingly, in this embodiment, the output of sensor pair 606 is preferably indicative of an accumulation of inorganic contaminant mass at measurement sensor 126a. It will be appreciated that selectivity for other contaminants and/or other categories of contaminants may be achieved with appropriate filter media and/or chemically selective membrane selection.

With reference to FIGS. 9-11, the operation of gas flow monitoring system 900 is presented below. Pressurized gas preferably enters monitoring system 900 through gas inlet fitting 906 and flows under pressure through tubing 910 and out of monitoring system 900 through gas outlet fitting 908. Monitoring system 900 preferably monitors non-toxic gases such as nitrogen and ambient air, but may monitor any other gases as well. The gas flow rate through tubing 910 is preferably between 0.1 cubic feet per minute (CFM) and 1.0 CFM. However, gas flow rates above and below this range may also be employed. The temperature of gas flowing in tubing 910 is preferably at the same temperature as the ambient air, that is, generally at "room temperature". However, monitoring system 900 may monitor gas at any temperature. The pressure of gas in tubing 910 is preferably between ambient pressure, which is preferably about 14 pounds per square inch (P.S.I.), and 100 P.S.I. However, monitoring system 900 may monitor gas at pressures above or below the stated pressure range.

Preferably, at gap 924 in tubing 910 the flowed gas is permitted to diffuse along filter inlet channel 918 through filter inlet 914 to filter 912. Once within filter 912, diffused gas preferably flows along diffusion path 930 around baffle 926, and through filter outlet 928. Diffused gas then preferably leaves filter 912, proceeds along filter outlet channel 922, and migrates toward reference sensor 124. Molecular contaminants within diffused gas 933 may then interact with the surface of reference sensor 124.

Preferably, measurement sensor 126 is exposed to an unfiltered flow of diffused gas. As with monitoring system 100, the difference between the signal outputs of reference sensor 124 and measurement sensor 126 is preferably indicative of the contaminant material trapped within filter 912. In an alternative embodiment, a filter (not shown), having a different filter medium than filter 912, may be deployed in the flow of diffused gas to measurement sensor 126.

There has been described a novel system and method for measuring molecular contaminants. Several embodiments of the system according to the invention have been described. It should be understood that each of the different embodiments may be combined with other embodiments to create different combinations, all of which have not been shown or described so as not to make the specification unnecessarily long. Clearly, now that the invention has been disclosed, those skilled in the art will be able to make other embodiments. Therefore, it should be understood that the particular embodiments shown in the drawings and described within this specification are for purposes of example and should not be construed to limit the invention which will be described in the claims below.

The invention claimed is:

1. A molecular monitoring system comprising:
    a piezoelectric measurement sensor exposed to a measurement environment;
    a piezoelectric reference sensor;
    a first filter located between said reference sensor and said measurement environment;
    said reference sensor being positioned so that it is exposed to essentially the same environment as said measurement sensor except for the portion of said environment that is filtered by said first filter;
    a second filter, having different selectivity than said first filter, located between said measurement sensor and said measurement environment; and
    output electronics electrically connected to said measurement sensor and said reference sensor for providing an output signal characteristic of a constituent of a molecular accumulation on said measurement sensor.

2. The system of claim 1 wherein said first filter is a chemical filter.

3. The system of claim 1 wherein said reference sensor is exposed to the pressure of said measurement environment.

4. The system of claim 1 wherein said reference sensor is exposed to the humidity of said measurement environment.

5. The system of claim 1 wherein said measurement sensor or said reference sensor comprises a SAW sensor.

6. The system of claim 1 wherein said measurement sensor or said reference sensor comprises a QCM sensor.

7. The system of claim 1 wherein there are a plurality of said measurement sensors.

8. The system of claim 1 wherein there are a plurality of said first filters and a plurality of said reference sensors, each of reference sensor associated with a different one of said first filters which is located between said measurement environment and said associated reference sensor.

9. The system of claim 1 wherein said first filter comprises a filter medium.

10. The system of claim 9 wherein said filter medium comprises charcoal.

11. The system of claim 9 wherein said filter medium comprises activated charcoal.

12. The system of claim 9 wherein said filter medium comprises doped activated charcoal.

13. The system of claim 9 wherein said filter medium comprises silicon.

14. The system of claim 9 wherein said filter medium comprises a porous polymer based on 2,6-diphenyl-p-phenylene oxide.

15. The system of claim 12 wherein said first filter comprises a multi-sorbent filtration media.

16. The system of claim 1 wherein said first filter comprises a chemically selective membrane.

17. The system of claim 16 wherein said chemically selective membrane comprises a thin film polymeric material.

18. The system of claim 16 wherein said chemically selective membrane comprises expanded polytetrafluoroethylene.

19. The system of claim 16 wherein said chemically selective membrane comprises a perfluorosulfonic acid polymer.

20. The system of claim 1 wherein said measurement environment comprises a vacuum environment or an ambient air environment.

21. The system of claim 1 wherein said measurement environment comprises a pressurized gas flow environment.

* * * * *